United States Patent
Collado et al.

(10) Patent No.: US 9,424,727 B2
(45) Date of Patent: Aug. 23, 2016

(54) BABY SLEEPING POSITION REMINDER

(71) Applicants: Irene Collado, Miami Beach, FL (US); David Collado, Miami Beach, FL (US)

(72) Inventors: Irene Collado, Miami Beach, FL (US); David Collado, Miami Beach, FL (US)

( * ) Notice: Subject to any disclaimer, the term of this patent is extended or adjusted under 35 U.S.C. 154(b) by 0 days.

(21) Appl. No.: 14/831,821

(22) Filed: Aug. 20, 2015

(65) Prior Publication Data

US 2016/0093189 A1 Mar. 31, 2016

Related U.S. Application Data

(63) Continuation-in-part of application No. 14/500,157, filed on Sep. 29, 2014, now abandoned.

(51) Int. Cl.
| | |
|---|---|
| *G08B 21/02* | (2006.01) |
| *G08B 21/24* | (2006.01) |
| *A61B 5/11* | (2006.01) |
| *G04F 1/00* | (2006.01) |
| *G04G 11/00* | (2006.01) |
| *A61B 5/00* | (2006.01) |
| *G08B 5/36* | (2006.01) |

(52) U.S. Cl.
CPC .............. *G08B 21/02* (2013.01); *A61B 5/1116* (2013.01); *A61B 5/6893* (2013.01); *G04F 1/005* (2013.01); *G04G 11/00* (2013.01); *A61B 5/1128* (2013.01); *A61B 5/6891* (2013.01); *A61B 2503/045* (2013.01); *G08B 5/36* (2013.01)

(58) Field of Classification Search
CPC ....... G04G 11/00; G04F 1/005; G04F 3/0484; G08B 5/36
USPC .................................................. 368/107–109
See application file for complete search history.

(56) References Cited

U.S. PATENT DOCUMENTS

| | | | | |
|---|---|---|---|---|
| 4,975,842 | A * | 12/1990 | Darrow ................. | G06F 19/322 128/923 |
| 5,583,832 | A * | 12/1996 | DePonty ............... | A61J 7/0472 307/141.4 |
| 5,854,774 | A * | 12/1998 | Timme ................... | G04G 17/08 368/10 |
| 6,014,346 | A * | 1/2000 | Malone ................ | A61B 5/1118 340/573.1 |
| 6,377,177 | B1 * | 4/2002 | Broussard .............. | G01G 19/44 340/309.7 |
| 7,835,230 | B1 * | 11/2010 | Chang .................. | G04G 15/006 368/109 |
| 7,916,036 | B1 * | 3/2011 | Pope ........................ | G04F 3/06 200/85 A |
| 8,094,013 | B1 * | 1/2012 | Lee ....................... | A61B 5/1116 340/539.15 |
| 2006/0123552 | A1 * | 6/2006 | Ben-Levi ............... | A61G 7/001 5/715 |
| 2010/0118659 | A1 * | 5/2010 | Orme ..................... | G04G 15/00 368/10 |
| 2012/0057433 | A1 * | 3/2012 | Diduch .................. | A61B 5/447 368/10 |
| 2013/0182541 | A1 * | 7/2013 | Diduch .................. | A61G 7/057 368/21 |

\* cited by examiner

*Primary Examiner* — Amy Cohen Johnson
*Assistant Examiner* — Matthew Powell
(74) *Attorney, Agent, or Firm* — David Michael Collado

(57) ABSTRACT

A device and method to remind parents to regularly alternate the head position of a sleeping baby in order to prevent or minimize positional plagiocephaly. The device comprises a display area displaying a plurality of suggested head positions and at least one user-selectable indicator for selecting a first one of said plurality of suggested head positions. The user-selectable indicator is coupled with a source of illumination for maintaining visual indication of said first head position until the user manually selects a second head position or the device is turned off. The device further comprises a processor coupled with memory configured to store the user-selected head position which is visually indicated upon deactivation of said source illumination. The processor can then be configured to cause said source of illumination to blink indicating the user-selected head position stored in said memory upon the device being powered on.

20 Claims, 11 Drawing Sheets

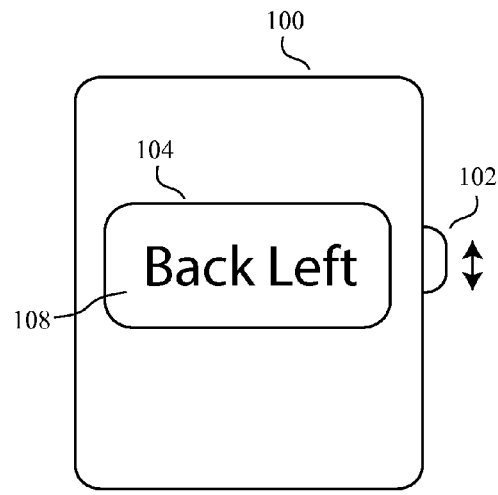
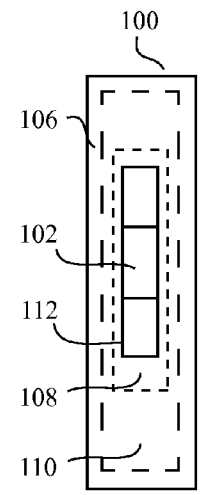
Fig. 5         Fig. 6
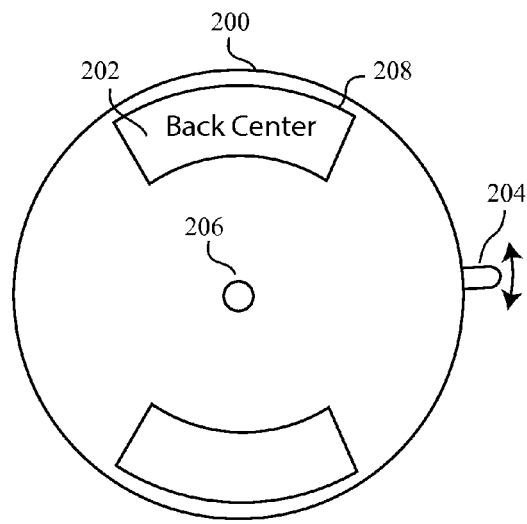
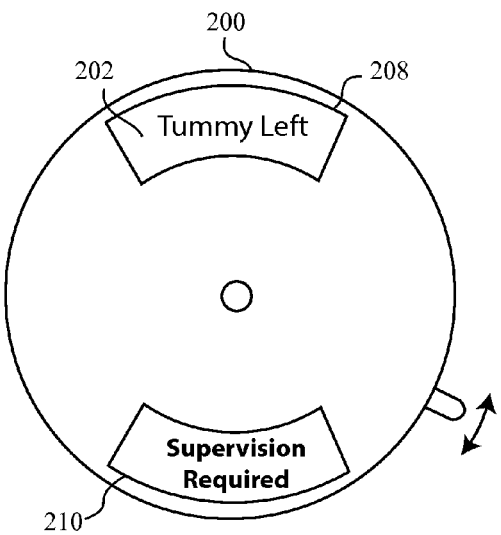
Fig. 7         Fig. 8

BABY SLEEPING POSITION REMINDER

CROSS REFERENCE TO RELATED APPLICATIONS

The present application is a continuation-in-part claiming priority to U.S. Non-provisional patent application Ser. No. 14/500,157, filed Sep. 29, 2014, entitled "Baby Sleeping Position Reminder" (herein referred to as "Parent application"). Parent application claims priority to U.S. Provisional Patent Application No. 61/895,523 filed on Oct. 25, 2013, U.S. Provisional Patent Application No. 61/929,945 filed on Jan. 21, 2014, and U.S. Provisional Patent Application No. 62/050,281 filed on Sep. 15, 2014, all of which are hereby incorporated by reference.

FIELD OF THE INVENTION

The present invention relates to a device for reminding caregivers to alternate the resting body position of newborns in order to minimize positional plagiocephaly, also known as "flat spots."

BACKGROUND OF THE INVENTION

Positional plagiocephaly is a condition which causes the back and/or sides of an infant's head to become flattened through prolonged pressure from resting on flat surfaces (such as in car seats, cribs, strollers, and playpens). The condition primarily affects newborns because the skull bones are softest immediately after birth and harden over time.

Positional plagiocephaly has become more prevalent in recent years due to the popular "Back To Sleep" campaign (BTS) promoted by pediatricians to minimize Sudden Infant Death Syndrome (SIDS). The BTS campaign instructs caregivers to lay infants to sleep on their backs and on firm mattresses. While BTS has succeeded in reducing the incidence of SIDS, it has exacerbated positional plagiocephaly because more babies are placed on their backs for prolonged periods of time on firm surfaces.

Positional plagiocephaly can be minimized by frequently alternating the baby's resting position so that the baby's head does not rest on any one side for excessive periods of time consecutively, or repeatedly without alternating positions in between. The goal is to even out the pressures on the baby's head in order to maintain roundness and avoid flattening. This recommendation is endorsed by the American Academy of Pediatrics (AAP). In fact, many hospital Neonatal Intensive Care Units (NICUs), which care for premature newborns, instruct nurses to rotate newborns' heads approximately every three hours.

Despite such knowledge, the problem persists. For example, on Jul. 8, 2013, the Huffington Post published an article titled "Nearly Half Of Babies Now Have 'Flat Spots' On Their Heads." The article cites a Canadian study published in the medical journal *Pediatrics* which found that "more than 46 percent of 2- to 3-month-old babies may have some form of the condition."

One of the causes is forgetful caregivers. New parents can be especially distracted and forgetful such that giving instructions alone will not sufficiently ensure the instructions are followed. With busy lives and other children and family members diverting their attention, parents with the best of intentions can still forget to alternate their baby's sleeping position. And even if they do remember to alternate their baby's sleeping positions, parents can still forget which position was chosen previously in order to choose a different position the next time the baby is laid to sleep.

Some have attempted to solve the problem with handwritten journals or logbooks. But these methods also suffer the problem of forgetful caregivers. Since parents have a hard time remembering instructions in the first place, they also have a hard time remembering to manually log their baby's sleeping position each and every time the baby sleeps, which can be six or more times each day. And even if a log book is used sometimes, the process is cumbersome and likely to be disregarded with some regularity.

Others have tried to solve the problem with specially designed soft pillows. These methods are problematic because the AAP suggests that no soft objects, specifically including pillows, should be left in a crib with a sleeping baby.

Though often the problem may be mild, and pediatricians may recommend no intervention because the condition can correct itself with time, parents nevertheless can suffer emotional distress and guilt from knowing that the condition could have been avoided by regularly alternating their baby's sleeping position.

But in other cases, intervention is advised. For example, in a not insignificant number of cases, custom molded helmets are used to reshape the baby's head which imposes additional emotional and financial costs on parents. Even here, however, there are issues. A New York Times article in May, 2014, titled *Helmets Do Little to Help Moderate Infant Skull Flattening, Study Finds*, revealed that these helmets may not be useful.

Accordingly, is it considered that there is a long felt need in the baby care field for a preventative solution to eliminate or reduce the incidence of positional plagiocephaly in a way which conforms with AAP guidelines.

SUMMARY OF THE INVENTION

The present invention aims to provide parents and caregivers with an effective reminder to alternate their baby's sleeping position each time the baby sleeps. The primary function of the device is to allow a parent/caregiver to selectively indicate a first resting head position when the baby is laid to rest, and thereby remind the parent/caregiver to subsequently choose a different resting head position the next time the baby is laid to rest. Head positions may include, for example, "Back Left," "Back Center," and "Back Right." While head position is the primary concern with preventing positional plagiocephaly, the present invention can also be used more broadly for reminding parents about overall body positions, such as "tummy time."

A common embodiment of the present invention comprises a device for regulating and monitoring infant head positions. The device comprises a body and power source, said body having a display area displaying a plurality of suggested head positions for the infant. The body also includes at least one user-selectable indicator for selecting a first one of said plurality of suggested head positions representing an actual head position of the infant at a first instance. The user-selectable indicator is coupled with a source of illumination for maintaining visual indication of said first one of said plurality of suggested head positions of the infant until the user manually selects a second one of said plurality of suggested head positions representing an actual head position of the infant at a second instance. The device further comprises a processor coupled with memory. The memory can be configured to store the user-selected head position which is visually indicated upon deactivation of said visual indication. For example, if the "back center" position is indicated immediately prior to the source of illumination being deactivated for whatever reason, then the memory will store the "back center" position. The processor can then be configured to cause said source of illumination to blink indicating the user-selected head position stored in said memory upon the device being powered on, said blinking to continue until the user manually selects a different head position.

The device may also be configured to turn off the source of illumination automatically, using either the processor and/or discrete circuitry, in order to conserve battery power. The user can then power the device back to an on state using a power button/switch or optional "reminder button," either of which will cause said source of illumination to indicate, through continuous or blinking illumination, the user-selected head position stored in said memory upon said power or reminder button being pressed.

For example, if the user places the infant to sleep at a first instance with a head position of "back center", the user will cause the user-selectable indicator to illuminate the "back center" head position on the device's display area. At this point the user can walk away knowing that she will be reminded at a later time which head position she chose at this first instance. The illumination will continue to indicate the "back center" position until either (Scenario 1) the user chooses a new position at a later instance, or (Scenario 2) the user manually powers off the device using a power button/switch, or (Scenario 3) the processor or discrete circuitry causes the illumination to deactivate after some predetermined amount of time (i.e., 5, 10, 15 minutes) in order to conserve power. Under Scenarios 2 and 3, a memory will store the user-selected head position which was selected at the time the illumination deactivated in order to enable the device to renew indication of that same head position when the user either powers the device on using a power button/switch or presses a reminder button.

To further enhance the reminding function of the device and compel the user to choose a new head position each time the infant is placed to rest, the processor can cause the source of illumination to blink when indicating the memory-stored head position upon the device being powered on or a reminder button being pressed. Following the example in the above paragraph, when the user returns to place the infant to rest at a second instance, the user can either (Scenario 1) see the visual indication of the "back center" position and thereby be reminded to choose a different head position for the infant's next sleeping session which begins at the second instance, or (Scenarios 2 and 3) press a "power" or "reminder" button which powers on the device and causes the source of illumination to blink indicating the memory-stored "back center" head position which in turn reminds the user to choose a different head position for the infant's next sleeping session which begins at the second instance.

The user interface can comprise one or more user-selectable indicators which enable the user to select one of a plurality of suggested head positions. A single user-selectable indicator can be used in configurations featuring a single button, or a multi-position switch or knob. Multiple user-selectable indicators can be used in configurations featuring a plurality of buttons, each button representing one of the plurality of suggested head positions. Moreover, these user-selectable indicators can optionally illuminate upon selection, Another optional feature envisioned for the present invention is a processor, said processor being configured to cause the illumination of a selected indicator to blink after a predetermined amount of time (60, 90, 180 minutes).

Another possible configuration for the user interface can comprise graphical/textual representations of a plurality of suggested body positions and a button which causes a different one of the plurality of suggested body positions to illuminate each time the button is pressed.

As an alternative to the user selecting one of the suggested body positions, a processor can automatically cycle through the suggested body positions by automatically illuminating a different one of said plurality of suggested body positions after a predetermined amount of time.

Regardless of the specific embodiment, illumination can be used to enhance the reminding function of the device whereby the selectively indicated body position is indicated by an illuminated lamp/LED which serves to remind the parent/caregiver to choose a different body position at a later time. This function can be enhanced by causing the illumination to blink after a predetermined amount of time to signal to the user that a new body position should be chosen for the baby's next sleeping session. An optional memory can be incorporated to store the most recently selected body position such that the device, if turned off and then on again, will default to the previous selected body position. Using a microprocessor coupled with the memory module, the illumination can be caused to blink upon the device being turned on in order to enhance the reminding effect of the illumination so that the user knows to choose a new body position. The memory module can also be used to maintain a log file of selected body positions and durations which can be communicated to mobile devices via an optional wireless communications module.

Another embodiment of the invention comprises a first object with an indicating shape and a second object displaying a plurality of suggested body positions whereby one of the plurality of suggested body positions can be selected by moving said first or second object such that the indicating shape aligns with the selected body position. This embodiment can also employ illumination with an optional processor to cause blinking as discussed above.

Another embodiment of the invention includes a wireless communications module configured to communicate selected body or head positions (and associated times) with one or more mobile devices. One such mobile device could be a smartphone running an application which mimics the functionality of the device, as described herein, through software. This embodiment would allow a user to enjoy the functionality of the device anywhere the user takes the smartphone while also ensuring continuity between the device and the smartphone application. Such a software application can also be used to maintain a log of selected body positions and times, allowing the user to monitor cumulative times for each position. Using wireless communications, such as WiFi or Bluetooth, multiple reminder devices can remain synchronized so that multiple reminder devices can be controlled by the mobile application. For example, one reminder device can be attached to a crib in the nursery room and another reminder device can be attached to a playpen in the living room. Both reminder devices can be in wireless communication with a mobile device application so that any sleeping position selection made by the user will appear on both reminder devices simultaneously. Similarly, when a sleeping position is selected on one of the reminder devices, the mobile application will be updated as will any other reminder devices. Consequently, when the mobile application is properly synchronized with one or more reminder devices, a user may leave the home with mobile application in hand and continue using the reminder functionality in continuity with the home-based reminders which can re-synchronize with the mobile application when the user returns home.

Additional embodiments of the invention include an analog or digital display for displaying the selected body or head position to the user. In the case of a digital display with touchscreen functionality, the display can also display the plurality of available head positions in addition to the selected head position, allowing the user to select a head position by touching the screen in the corresponding location. The digital display embodiments would also include a processor to control the display.

Examples of digital displays include LED, LCD, OLED and TFT displays (with or without backlight), but it is understood that any type of digital display can be used. Examples of non-digital displays include backlit transparencies, illuminating buttons, dry-erase surface and marker, and moving, sliding, rotating or hinged objects representing the sleeping positions to be selected. It is understood that any means of allowing a user to selectively indicate one of a plurality of suggested body positions, and thereafter identify which body position was selected, can be used as a display.

Another embodiment of the invention uses sensors to determine a resting baby's body position. The sensor can comprise a camera and image analysis software. The sensor can determine with which head position the baby is resting at any given time and, coupled with a processor and memory, record a log of head positions and cumulative times the baby rested in each position. The sensor can also enable the device to alert the parent/caregiver if the baby moves his/her head to a position which differs from the selected position chosen by the parent/caregiver.

While the preferred embodiment enables the user to selectively indicate one of a plurality of suggested body positions, another embodiment can rely on a timer to cycle through a plurality of suggested body positions and thereby act as an affirmative instruction to the user which position to choose for the resting baby at any given time.

The present invention also covers a method for regulating and monitoring infant head positions. The method comprises (1) providing a body having a display area displaying a plurality of suggested head positions for the infant; (2) selecting manually from the plurality of suggested head positions, using a user-selectable indicator, a first actual head position representing the actual head position in which the infant is placed to rest at a first instance; (3) maintaining visual indication, using a source of illumination, of said first actual head position until the user manually selects, using the user-selectable indicator, a second one of the plurality of suggested head positions representing the actual head position in which the infant is placed to rest at a second instance; (4) storing in memory the user-selected head position which is visually indicated upon deactivation of said visual indication; and (5) causing said source of illumination to blink indicating the user-selected head position stored in said memory upon the device being powered on, said blinking to continue until the user manually selects a different head position using the user-selectable indicator.

The method for presenting to the user a plurality of suggested body positions can comprise a plurality of buttons, each button corresponding to a body position. It can also comprise a display area with graphical and/or textual representations of the suggested body positions, or a digital display depicting the same.

The method for providing a visual cue to the user can comprise illumination associated with a selected body position, such as by lighting an LED or lamp. It can also comprise a digital display displaying a previously selected body position or a suggested body position. Generally speaking, the method of selecting a first body position at a first instance will visually distinguish said first body position from the remaining unselected body positions, and this visual distinction will serve as the visual cue to remind the user to choose a different body position at a later instance.

The method for selecting a body position can comprise pushing a button, switching a switch or turning a knob. It can also comprise touching a touchscreen. It can also comprise moving a first object with an indicating shape (like an arrow or window) into alignment with a second object displaying a plurality of suggested body positions such that the indicating shape aligns with the selected body position.

The method can further incorporate a step whereby the source of illumination deactivates after a predetermined amount of time. Said predetermined amount of time can be 5, 10, 15, 20 or 30 minutes.

The method can further comprise pressing a reminder button which causes said source of illumination to blink indicating the user-selected head position stored in said memory upon said reminder button being pressed.

The method can also comprise attaching said body to a baby crib using an integrated attachment mechanism configured for attachment of the body to a baby crib.

The method can also comprise storing in said memory a log of previous user-selected head positions, and communicating said log to one or more mobile devices via a wireless communications module Another aspect of the invention which may be common to all embodiments is the presence of one or more attachment mechanisms. Examples of suitable attachment mechanisms include adhesive, hooks, clamps, snaps, Velcro, nuts and bolts, and adjustable straps for easy attachment of the device to the types of railings and handles commonly found on cribs, car seats, playpens, strollers and other places babies often rest for prolonged periods of time. Alternatively, a separate holster or pouch can be used which affixes to the desired location and holds the device in place. Each of the possible attachment means can be configured to allow easy removal and portability if the user wants to use the device in multiple places. The objective of the attachment means is to enable convenient attachment of the device in the types of environments babies are commonly laid to sleep (e.g., cribs, playpens, strollers, car seats, etc.). Accordingly, another desirable feature of the present invention is a transparent cover (hard or soft) to protect the device from body fluids emanating from the baby (i.e., vomit, urine).

Any of the embodiments of the invention disclosed herein can be integrated into baby accessories (e.g., bags, blankets, bracelets, pillows, necklaces, carseats, strollers), clothing (e.g., hats, onesies, shirts, socks), furniture (e.g., cribs, playpens) and toys (e.g., mobiles, stuffed animals). The device can also be integrated into accessories for parents (e.g., bracelets, watches).

Ideally, weight should be kept to a minimum, within the constraints of the overall configuration, to facilitate convenient attachment in a variety of positions and locations. For example, to make attachment inside, or on the perimeter of, a crib or playpen, minimum weight is desirable to minimize stress on the attachment means and to minimize potential harm to the baby if the device falls inside the crib or playpen. Therefore, lightweight construction is desirable for embodiments designed for such attachment. Accordingly, integrating the device into a soft cushioned housing can also be a desirable configuration.

In another aspect of the device, a camera can be integrated into the device to stream audio/video signals to a remote monitor, including but not limited to a mobile computing device.

BRIEF DESCRIPTION OF THE DRAWINGS

FIG. 5 is a front view of a second embodiment of the present invention, wherein the second embodiment comprises a sliding selector;

FIG. 6 is a side view showing internal construction of the second embodiment of FIG. 5;

FIG. 7 is a front view of a third embodiment of the present invention, wherein the third embodiment comprises a rotating selector rotated to a first position;

FIG. 8 is a front view of the third embodiment of FIG. 7, showing the rotating selector rotated to a second position that is different than the first position shown in FIG. 7;

DETAILED DESCRIPTION OF THE PREFERRED EMBODIMENT

The present invention is a device and method for reminding parents and caregivers to alternate the sleeping position of a baby, as recommended by the American Academy of Pediatrics, in order to minimize positional plagiocephaly, commonly referred to as "flat spots."

It is understood by one having ordinary skill in the relevant art that all embodiments described herein requiring a power supply can use batteries, wall power, solar or other power source. Batteries can be replaceable and/or rechargeable by plugging the device into the wall through a mini-port (e.g., mini-USB).

Figure 1:
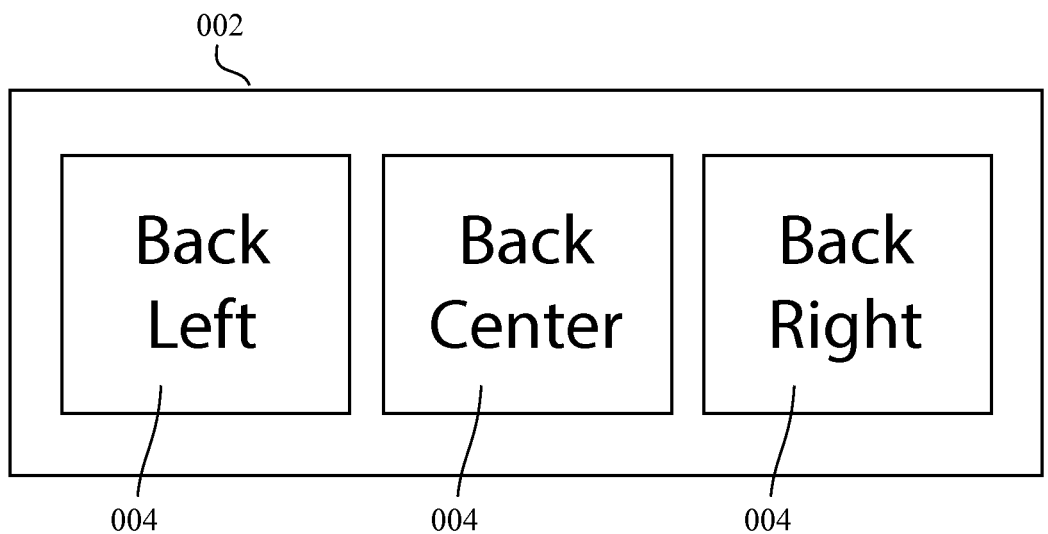
FIG. 1 is a front view of a first embodiment of the invention.

FIG. 1 illustrates an embodiment of the invention featuring a three-button user interface, comprising a plurality of illuminating buttons 004 which present to the user a plurality of suggested body positions. Buttons 004 can display either text alone (as shown), graphics, or text plus graphics. Housing 002 contains discrete circuitry and illumination means (shown in FIG. 3) which enable each button to illuminate upon being pressed, while de-illuminating the other two buttons so only one button is illuminated at any time. It is understood by one having ordinary skill in the relevant art that such ciruitry is elementary to implement. The illumination of the selected body position reminds the user which body position was selected for the baby's previous sleeping session, which in turn reminds the user to choose a different body position for the baby's next sleeping session.

Figure 2:
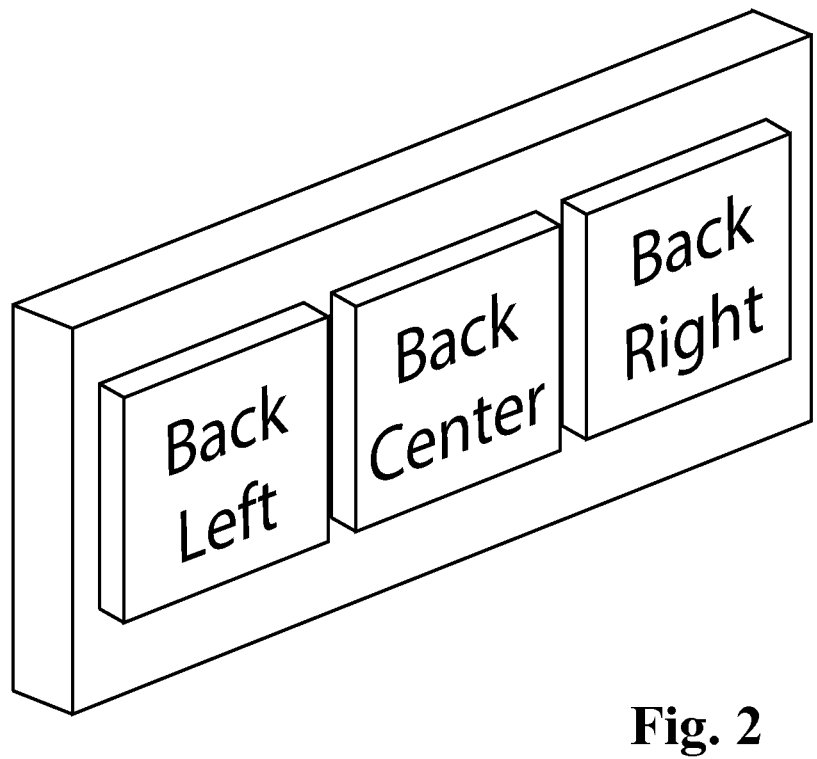
FIG. 2 is a perspective view of the first embodiment of FIG. 1.

FIG. 2 illustrates a perspective view of the embodiment in FIG. 1 to demonstrate a preferred, relatively thin, form factor for the device to minimize weight and facilitate versatile attachment in various settings.

Figure 3:
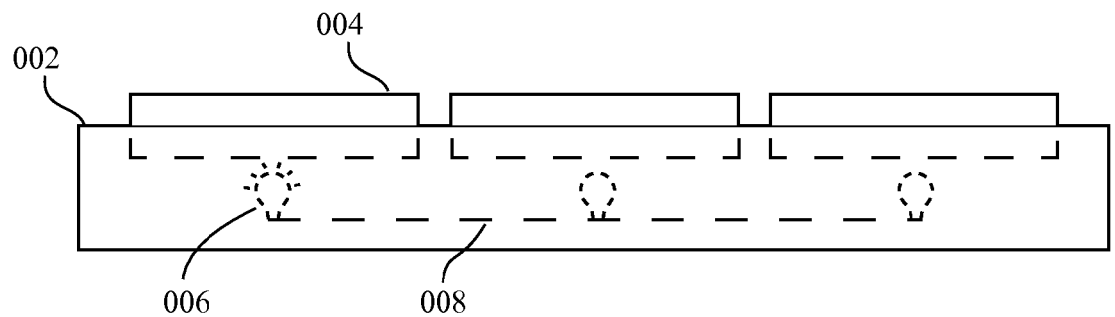
FIG. 3 is a first side view of the first embodiment of FIGS. 1 and 2, schematically illustrating optional illumination.

FIG. 3 illustrates a cross-sectional view showing illumination 006 and circuitry 008 disposed within housing 002. This view shows button 004 illuminated by illumination 006, and how the buttons can be partially disposed within housing 002 so that the buttons connect with circuitry 008. It is understood by one having ordinary skill in the relevant art that there are many different mechanisms for connecting buttons to circuits, so this element is not shown here for simplicity. Circuit 008 can also be configured with an optional processor (not shown) so that illumination 006 begins to blink after a predetermined amount of time (i.e. 30, 60 or 180 minutes). Another optional feature of this embodiment is a memory module to store the most recently selected body position. This memory function can be used to maintain a log of body positions and/or so the device can be turned off and then on again with the device defaulting to the most recently selected body position. It is understood by one having ordinary skill in the relevant art that implementing such a circuit, processor and memory module is elementary.

Figure 4:
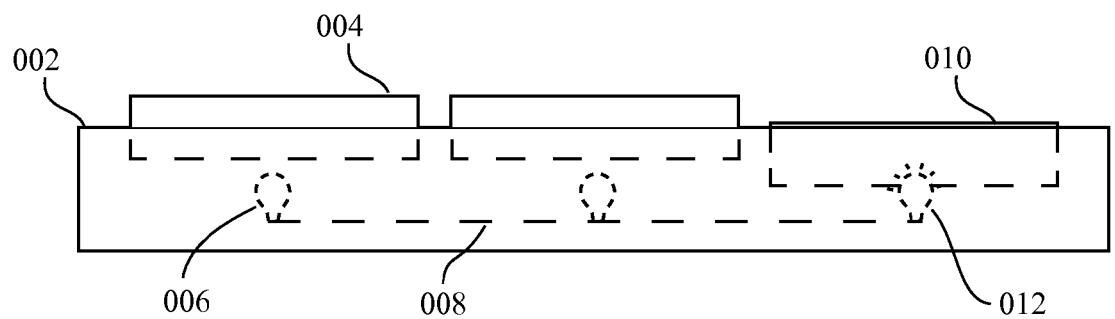
FIG. 4 is second side view of the first embodiment, showing a pressed button state.

FIG. 4 illustrates the same cross-sectional view in FIG. 3, but with button 010 in the pressed position. Notice that with button 010 pressed, illumination 012 illuminates and illumination 006 de-illuminates. When button 010 returns to its unpressed position, illumination 012 will remain the only source of illumination until a different button is pressed. It is understood by one having ordinary skill in the relevant art that implementing circuit 008 to enable the illumination scheme described herein is elementary.

The embodiment in FIGS. 1 through 4 are not limited to the construction of detail shown there or described in the accompanying text. As those of skill in the art will understand, the embodiment can be fabricated from any suitable material in any suitable dimensions using any suitable components which allow a user to select one of a plurality of suggested body positions at a first instance, and subsequently remember to select a different one of said plurality of suggested body positions when placing the baby to sleep at a later instance.

FIG. 5 illustrates an embodiment of the invention featuring a display window user interface with sliding selectable indicator which allows the user to select one of several suggested body positions by moving tab 102 which is attached to internal object 108. Housing 100 contains a display window 104 through which the user can view a portion of internal object 108 displaying a plurality of suggested body positions. By sliding tab 102 up or down, the user can cause a different one of the plurality of suggested body positions to be displayed through display window 104.

FIG. 6 illustrates a side-view of the embodiment in FIG. 5 to further show how tab 102 is attached to internal object 108 which is disposed inside cavity 110 of housing 100. By sliding tab 102 up or down within slot 112 in housing 100, object 108 can be repositioned inside cavity 110 such that a different body position displayed on object 108 can be viewed through window 104 as shown in FIG. 5. It is understood by one having ordinary skill in the relevant art how to manufacture an embodiment as depicted in FIGS. 5 and 6 with appropriate dimensions, tolerances and materials so that object 108 stays firmly in place after the user moves tab 102 up or down.

FIG. 7 illustrates another version of the display window user interface embodiment, this time in a circular configuration. A user of this embodiment can select one of several suggested body positions by sliding tab 204, which is attached to display wheel 202, along its arching range of motion. This embodiment comprises a cover wheel 200 and display wheel 202. Axel 206 (a rivet or other type of rotation-enabling fastener) allows cover wheel 200 and display wheel 202 to rotate around a common axis. Display wheel 202 displays a plurality of suggested body positions, each of which can be viewed by the user through display window 208 in cover wheel 200. For example, when the user wants to select the sleeping position "Back Center," the user can slide tab 204 in either direction until s/he sees "Back Center" displayed in display window 208.

FIG. 8 illustrates how certain suggested body positions displayed on display wheel 202, such as belly positions which pediatricians suggest parents should closely supervise, can be associated with special instructions to be displayed through a second display window 210 (special instructions can also be displayed through the same display window as the suggested body position). For sleeping positions without special instructions, such as in FIG. 7, the second display window 210 will remain empty because there will be no special instructions displayed on the corresponding portion of display wheel 202. For sleeping positions with special instructions, such as in FIG. 8, the special instructions will appear in display window 210 because they will be displayed on the corresponding portion of display wheel 202.

Figure 9:
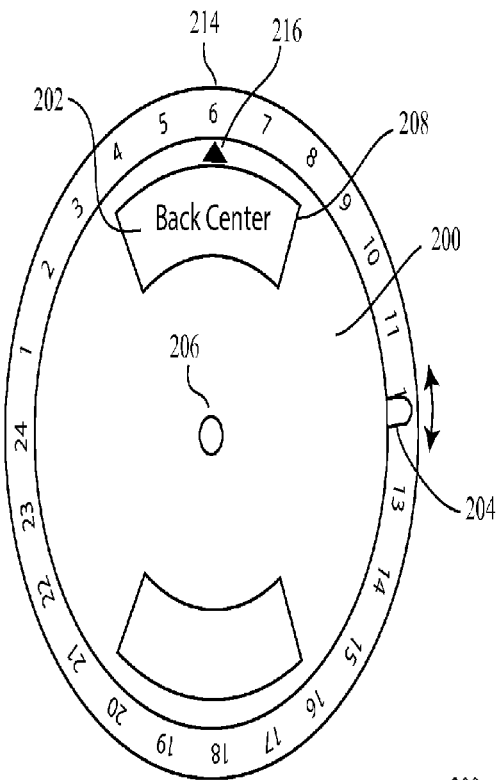
FIG. 9 is front view of a fourth embodiment of the invention comprising a rotating selector rotated to a first position, and a timekeeping wheel.

FIG. 9 illustrates another version of the rotating wheel user interface embodiment introduced in FIG. 7. This embodiment adds a time wheel 214 which allows the user to select the time of day that a sleeping position is selected. Time wheel 214 rotates independently around the same axis 206 as cover wheel 200 and display wheel 202. The user can rotate time wheel 214 so that the time of day aligns with indicator 216. By selecting a time of day each time a new sleeping position is chosen, the user can know when a new position should be chosen at a later instance. For example, if the user lays the baby to sleep and selects the "Back Center" position at 12 PM, and then lays the baby to sleep again at 6 PM, the user can observe that the "Back Center" position was chosen for the baby's last sleep session and therefore choose a different position for the baby's next sleep session.

Figure 10:
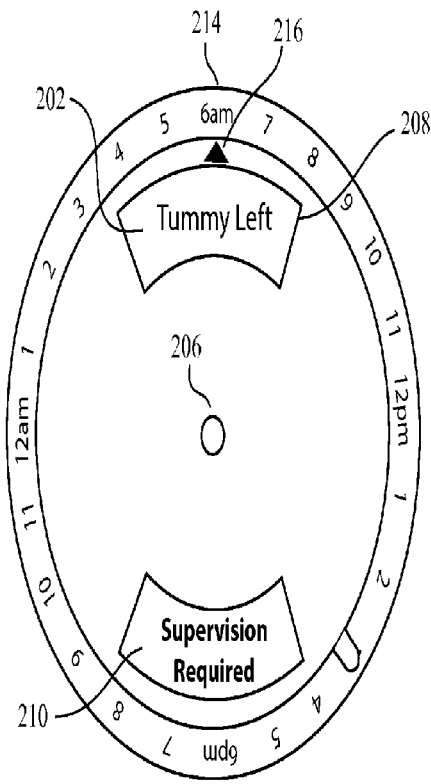
FIG. 10 is front view of the fourth embodiment of FIG. 9, showing the rotating selector rotated to a second position that is different than the first position shown in FIG. 9.

FIG. 10 shows the rotating wheel embodiment with time wheel introduced in FIG. 9, but with AM/PM time markings instead of military time (e.g., 0-24 hours) markings as in FIG. 9. FIG. 10 also illustrates the special instruction feature introduced in FIG. 8.

Figure 11:
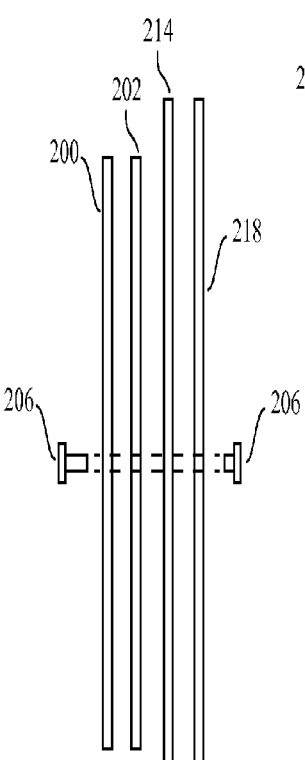
FIG. 11 is side exploded view schematically illustrating a possible construction for rotating selector embodiments of the present invention.

FIG. 11 illustrates a side exploded view of the embodiments in FIGS. 9 and 10 with an optional mounting piece 218. Axle 206 is shown in a two-piece configuration, but a single piece rivet or other type of rotation-enabling fastener can be used to hold the pieces together and provide a common axis around which pieces 200, 202 and 214 can rotate.

The embodiments of FIGS. 7 through 11 can be constructed with paper, laminated paper, plastic, or other lightweight material. Additionally, a mounting piece can be used—such that the display wheel is sandwiched between the cover wheel and mounting piece—to facilitate attaching, hanging or mounting of the device.

Figure 12:
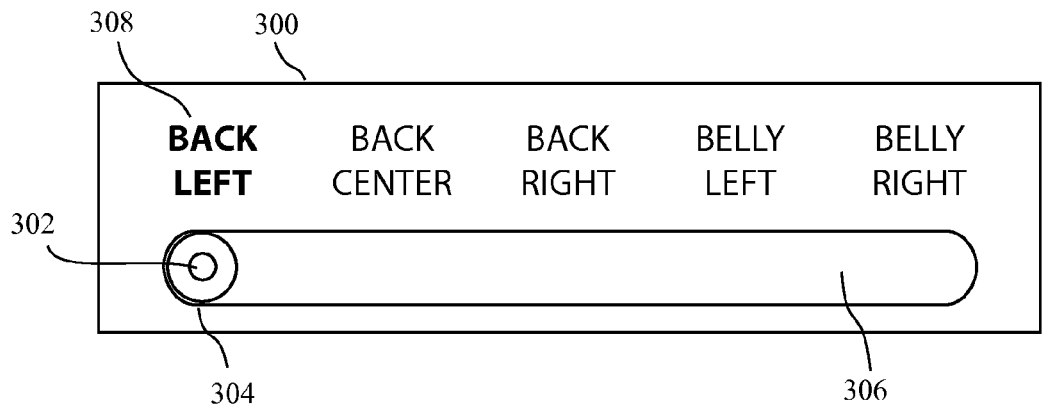
FIG. 12 is a front view of a fifth embodiment of the present invention.

FIG. 12 illustrates an embodiment of the invention featuring a multi-position switch user interface which allows the user to select one of several suggested body positions by sliding a multi-position switch 304 into a position which corresponds with one of a plurality of suggested body positions 308, the plurality of body positions being indicated by text (and/or images) displayed on housing 300. By sliding switch 304 along its range of motion 306, the user can select a different sleeping position, such as "Back Left" as indicated in FIG. 12. An optional LED 302 can be configured to illuminate each time a different position is selected. Additionally, LED 302 can be configured to blink after a selected body position has been selected for a predetermined amount of time (e.g., 30 minutes, 45 minutes, 1 hour, 3 hours). As in FIGS. 1 through 4, it is understood by one having ordinary skill in the relevant art that implementing the circuitry necessary for the illumination scheme described herein is elementary.

Figure 13:
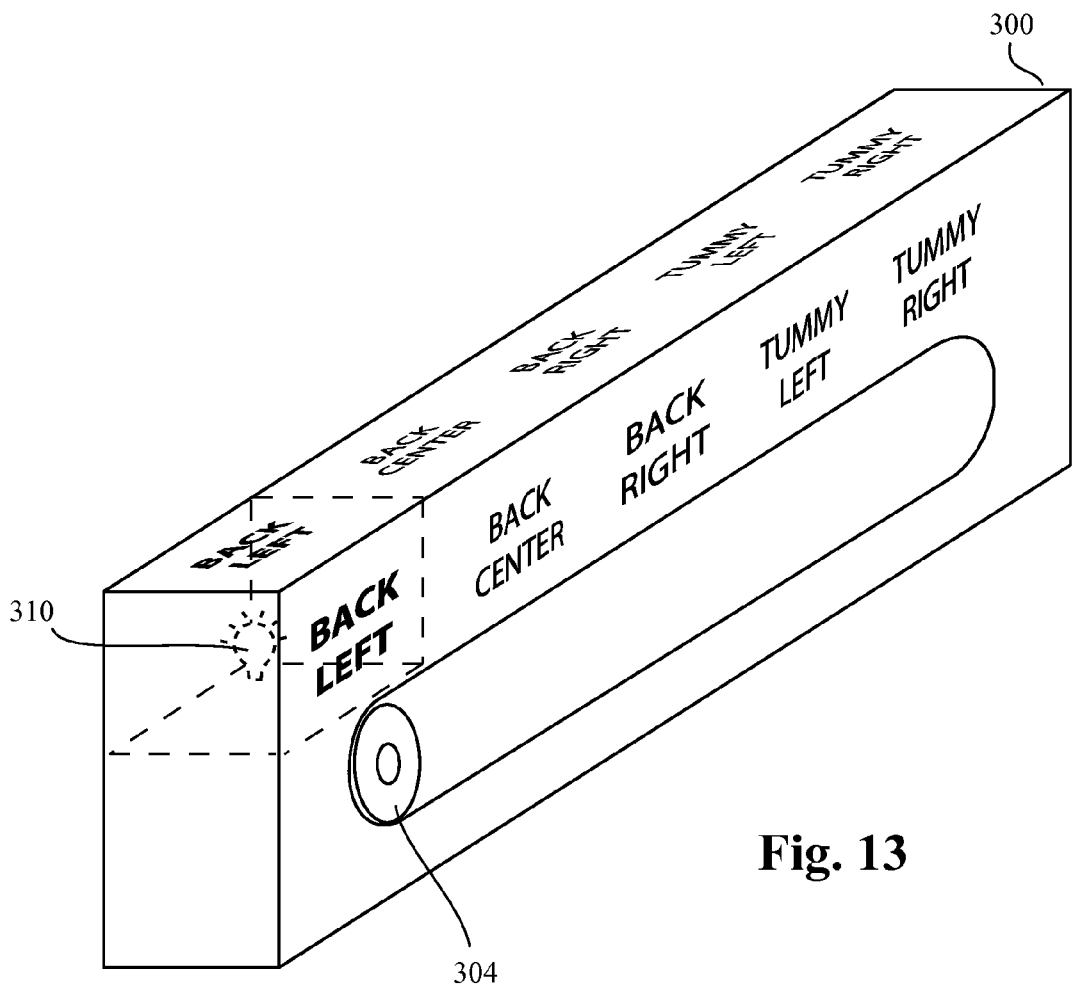
FIG. 13 is a perspective view of the fifth embodiment of FIG. 12, schematically illustrating optional illumination.

FIG. 13 illustrates a perspective view of the embodiment in FIG. 12 showing internal construction comprising illumination 310 which illuminates the user-selected body position to stand out against the unselected positions. A lamp (or LED) 310 disposed inside housing 300 behind each selectable body position can be illuminated upon the user placing switch 304 in the position corresponding to said body position. FIG. 13 also shows how the sleeping positions can be displayed on multiple surfaces of housing 300 to facilitate viewing from multiple angles. If affixed inside a crib, the user can more easily see the sleeping positions displayed along the device's top surface. If affixed to the railing, the side displays will be more visible.

Figure 14:
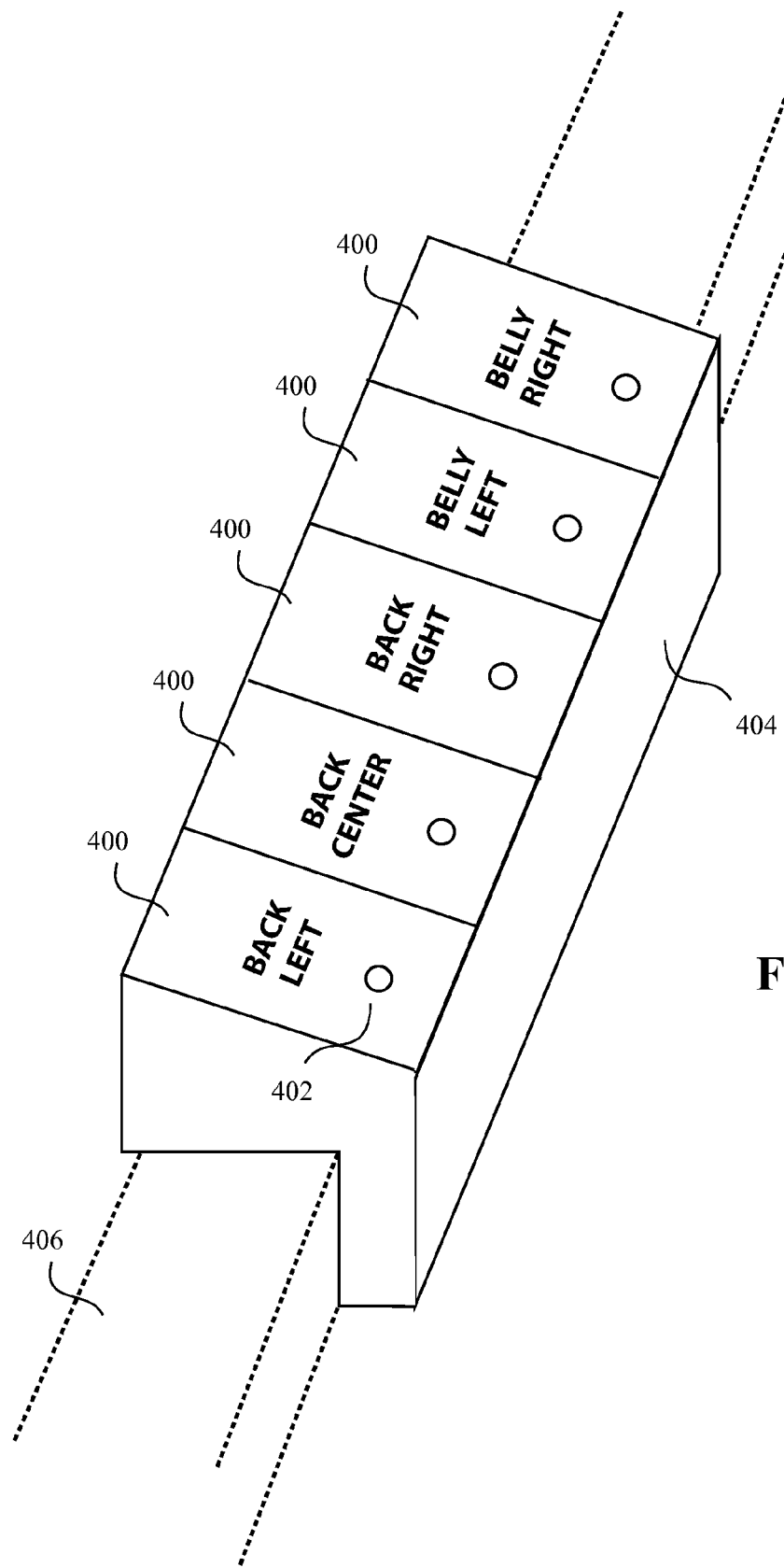
FIG. 14 is a perspective view of a sixth embodiment of the invention, where the sixth embodiment is attached to a crib or playpen railing.

FIG. 14 illustrates a perspective view of an embodiment adapted for attachment to the railing 406 of a crib or playpen. This embodiment has a 5-button user interface. Buttons 400, each one corresponding to a user-selectable suggested body position, are configured along an inclined surface of housing 404 for easy viewing and access to a typical adult user standing at the side of a crib or playpen. LED 402 (one on each button) can illuminate upon the pressing of a button, and optionally blink after a predetermined amount of time, as discussed previously.

Figure 15:
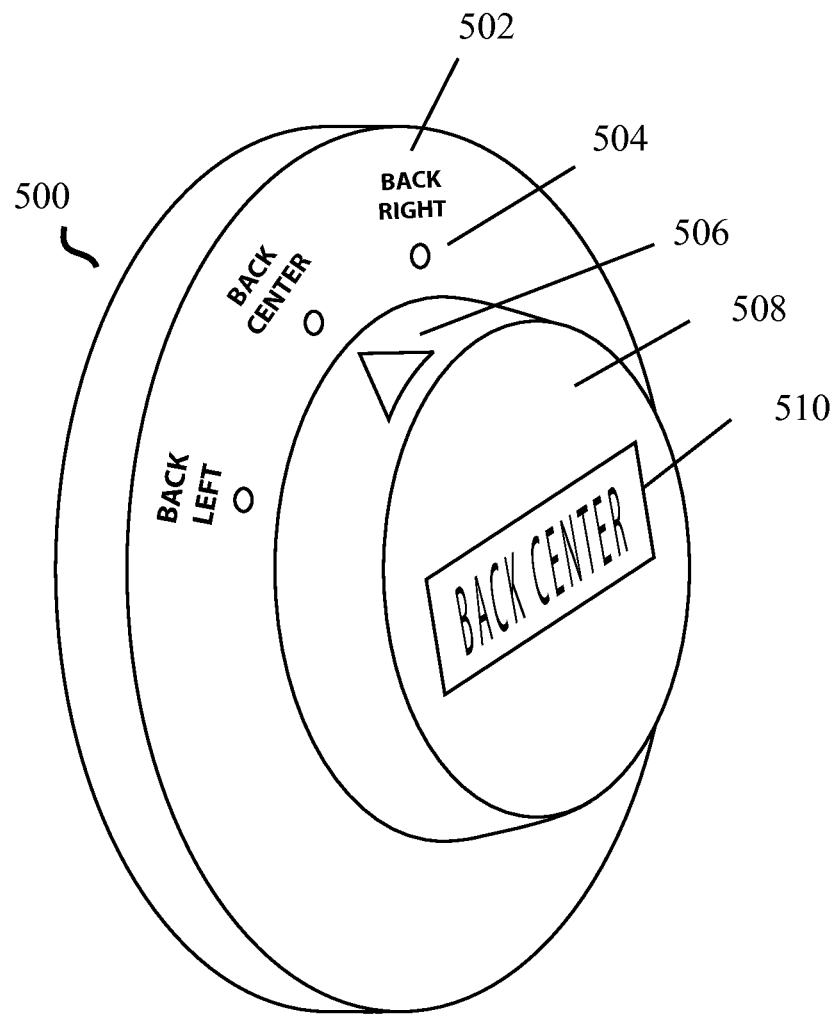
FIG. 15 shows a perspective view of a seventh embodiment of the invention, where the seventh embodiment includes a rotating selector.

FIG. 15 illustrates an embodiment of the present invention featuring a rotating knob user interface, which allows the user to select one of a plurality of suggested body positions by rotating selector 508. The user can select one of the body positions by rotating selector 508 such that indicator 506 aligns with one of the body positions 502 ("Back Left", "Back Center", "Back Right") displayed on body 500. The selected position can be further indicated by an optional LED 504 and/or optional digital display 510.

Figure 16:
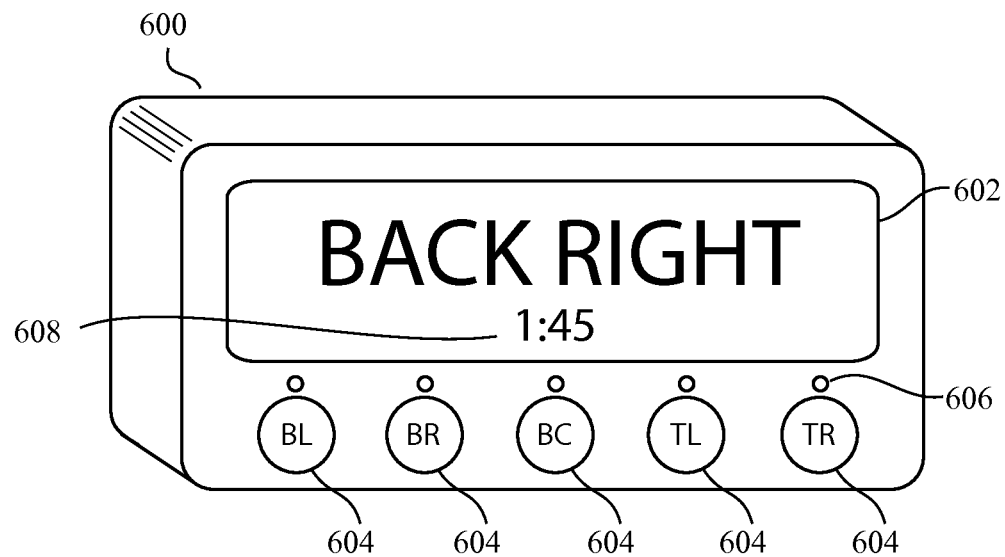
FIG. 16 shows a perspective view of an eighth embodiment of the present invention.

FIG. 16 illustrates a perspective view of an embodiment of the present invention featuring a digital display and multi-button user interface. This embodiment comprises a digital display 602 communicating a body position corresponding to the button 604 selected by the user (illustrated here as a series of buttons; but switches, sliders and knobs can be used). Optional timer 608 counts the time a given position is displayed. An optional LED 606 (one for each button) illuminates when the corresponding button/position is selected, and optionally blinks after a predetermined amount of time. Housing 600 contains the aforementioned components and an optional attachment mechanism (not shown) which allows the user to affix the device within the immediate vicinity of the baby's resting/sleeping environment (e.g., inside of a crib, railing of a playpen, handle of a car seat or stroller).

Figure 17:
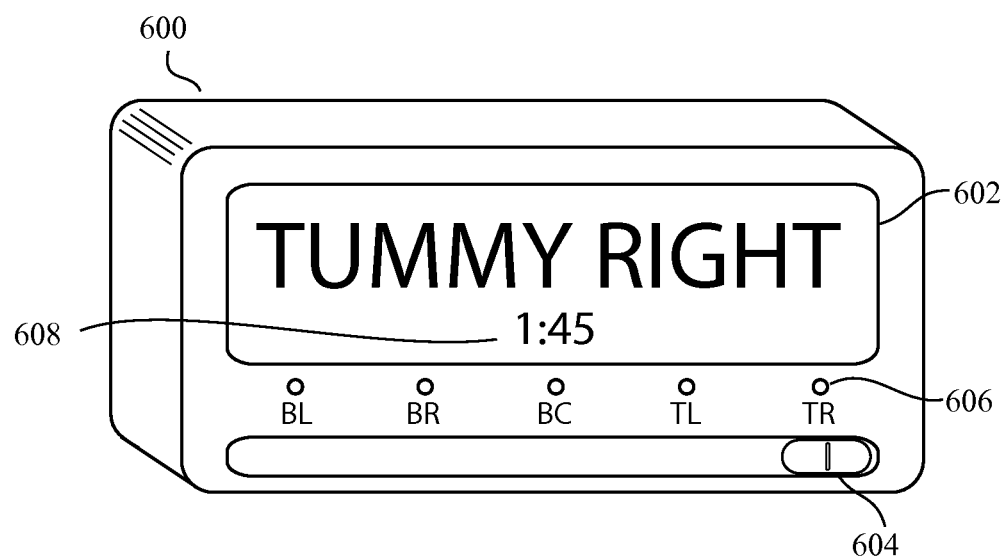
FIG. 17 illustrates a ninth embodiment of the present invention, in the form of the embodiment of FIG. 17 using a sliding switch selector instead of buttons.

FIG. 17 illustrates a perspective view of an embodiment of the present invention featuring a digital display and sliding multi-position switch user interface, similar to the embodiment in FIG. 16, but with a sliding multi-position switch 604 instead of individual buttons.

Figure 18:
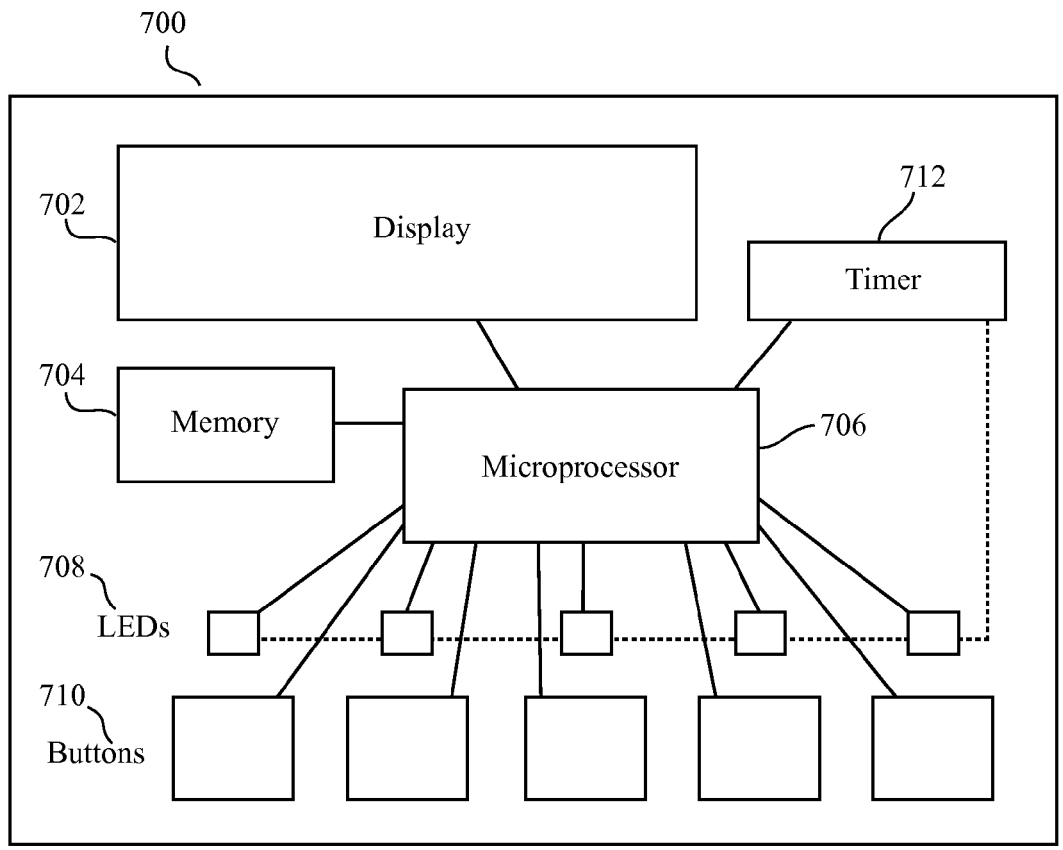
FIG. 18 schematically illustrates a possible configuration of internal components of embodiments of the present invention including a microprocessor.

FIG. 18 illustrates a schematic representation of the internal components of the embodiments in FIGS. 16 and 17. Buttons 710 correspond to the different body positions. When the user selects a button, microprocessor 706 sends the corresponding information from memory 704 to the digital display 702 such that the selected body position is displayed. Simultaneously, microprocessor 706 begins counting the time that the current position is displayed. The elapsed time can be displayed on digital display 702, a separate timer 712, or not be displayed at all. The LED 708 corresponding to the selected button 710 illuminates solidly upon being pressed by the user, and optionally begins to blink after a predetermined amount of time in order to inform the user that said amount of time has elapsed since the button was pressed. If the user selects a different button 710, the previously lit LED 708, whether solid or blinking, ceases illumination and the LED corresponding to the new button illuminates and the timer resets. The aforementioned functionality is controlled by the microprocessor, as programmed by a person having ordinary skills in the art of basic electronic processors, and/or through discrete circuitry as configured by a skilled electrical circuit designer.

Figure 19:
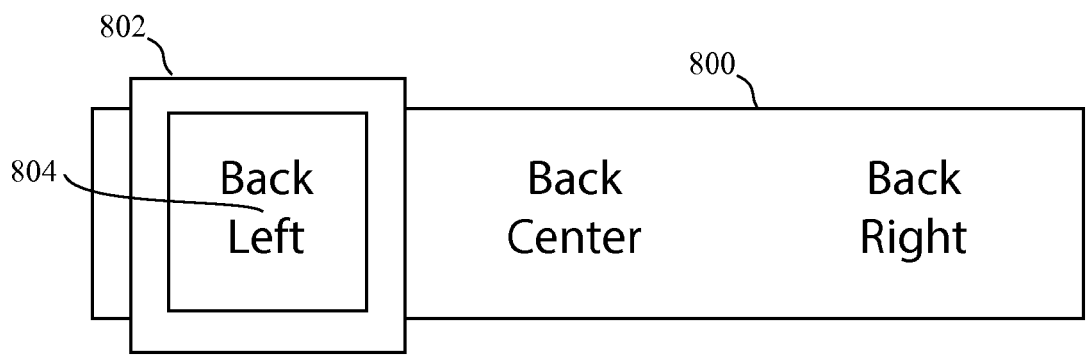
FIG. 19 is a front view of a tenth embodiment of the present invention.

FIG. 19 illustrates an embodiment of the invention featuring a display window user interface, comprising a first object 800 displaying a plurality of suggested sleeping positions 804, and a second object 802 with a display window through which the sleeping positions displayed on said first object 800 can be viewed. Alternatively, instead of a display window, second object 802 can feature a conspicuous indicating shape, such as an arrow or triangle, to point out the selected body position. By sliding second object 802 in relation to said first object 800, the user can align the window (or indicating shape) with the selected body position, and thereby selectively indicate a first body position when laying a baby to rest at a first instance. This indication then serves as a visual cue to remind the user to subsequently select a second body position different from said first body position when laying the baby to rest at a later instance.

Figure 20:
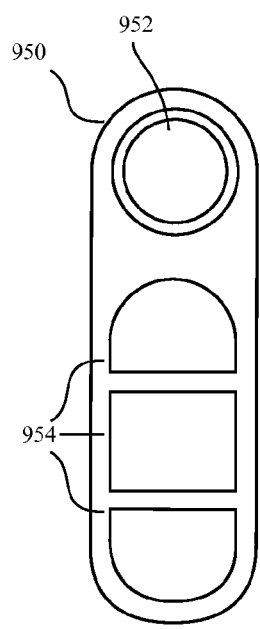
FIG. 20 is front view of an eleventh embodiment of the present invention.

FIG. 20 illustrates an alternative embodiment of the invention comprising a main housing 950 with illuminating buttons 954 disposed within said housing, wherein housing 950 is configured with a hole which allows the housing to be hung on a circular hook 952. The purpose of this figure is only to illustrate one of many possible attachment mechanisms for the device.

Figure 21:
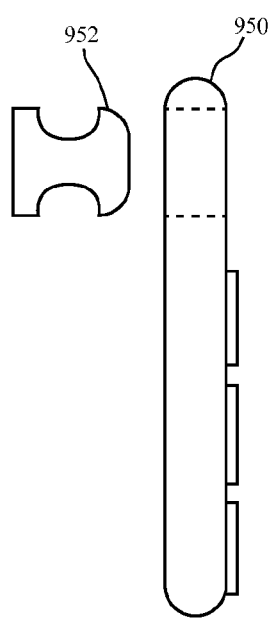
FIG. 21 is a side view of the eleventh embodiment of FIG. 20, illustrating how the eleventh embodiment may be mounted with a hanging knob attachment mechanism.

FIG. 21 illustrates a side view of the embodiment in FIG. 20 demonstrating how housing 950 can be hung on circular hook 952.

Figure 22:
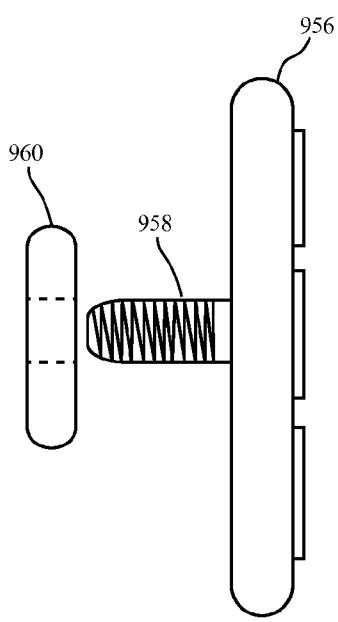
FIG. 22 is a side view of a twelfth embodiment illustrating how the device may be mounted with a screw clamp attachment mechanism.

FIG. 22 illustrates another embodiment of the present invention featuring a screw-clamp attachment mechanism. A main housing 956 (with buttons disposed within) is configured with a bolt 958 extending from the rear of the housing such that a user can attach the housing to a structure by screwing nut 960 onto the bolt such that the housing will be firmly held in place. The purpose of this figure is only to illustrate one of many possible attachment mechanisms for the device.

Figure 23:
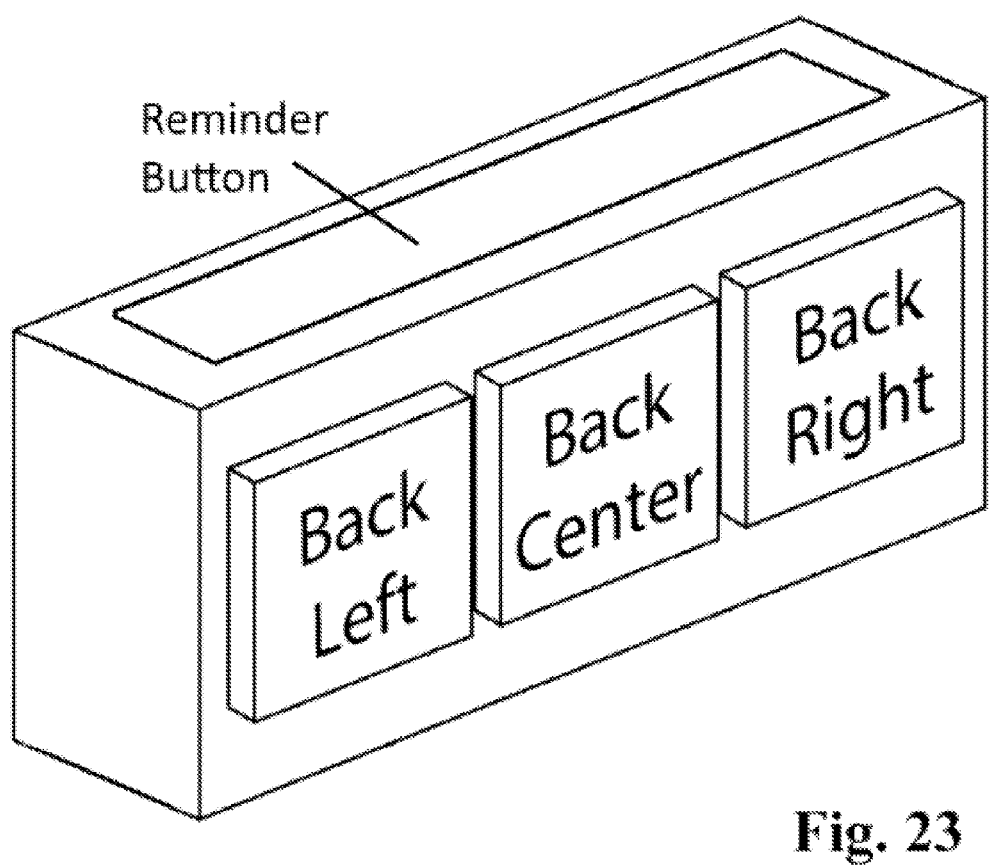
FIG. 23 is a perspective view of the embodiments in FIGS. 1 through 4 showing an optional "reminder button".

FIG. 23 illustrates another embodiment of the present invention (based primarily on the embodiment depicted in FIGS. 1 through 4) featuring a "reminder button" feature which is intended to provide the user with a large and conveniently placed button for the user to press in order to power the device on (when the device is in an off state) and cause the processor and memory to indicate the previous user-selected head position with a blinking source of illumination (as seen in FIGS. 3 and 4).

It will be appreciated that the specific orientations used within these Figures to demonstrate the apparatus functionality are by way of example only. Any attachment/detachment mechanism, such as those depicted in FIGS. 20-22, can also be used for any other compatible embodiment described herein.

The present disclosure is directed to each individual feature, system, material, and/or method described herein. In addition, any combination of two or more such features, systems, materials, and/or methods, if such features, systems, materials, and/or methods are not mutually inconsistent, is included within the scope of the present invention. To avoid undue repetition, not all features are discussed in conjunction with every aspect, embodiment or practice of the disclosure. Features described in conjunction with one aspect, embodiment or practice are deemed to be includable with others absent mutual inconsistency or a clear teaching to the contrary. In some instances, features will be discussed generally rather than in detail in conjunction with a specific aspect, embodiment or practice, and it is understood that such features can be included in any aspect, embodiment or practice, again absent mutual inconsistency or a clear teaching to the contrary.

The invention claimed is:

1. A device for regulating and monitoring infant head positions, the device comprising:
 a body;
 a power source;
 said body having a display area displaying a plurality of suggested head positions for the infant;
 said body including at least one user-selectable indicator for selecting a first one of said plurality of suggested head positions representing an actual head position of the infant at a first instance;
 said user-selectable indicator being coupled with a source of illumination for maintaining visual indication of said first one of said plurality of suggested head positions of the infant until the user manually selects a second one of said plurality of suggested head positions representing an actual head position of the infant at a second instance, or until the device is powered off;
 said source of illumination electrically connected to said power source;
 a processor coupled with memory;
 said memory configured to store the user-selected head position which is visually indicated at the time the device is powered off;
 said processor configured to cause said source of illumination to blink indicating the user-selected head position stored in said memory upon the device being powered on, said blinking to continue until the user manually selects a different head position or until the device is powered off;

a reminder button which causes said power source to cause said source of illumination to blink indicating the user-selected head position stored in said memory upon said reminder button being pressed.

2. The device as recited in claim 1 wherein the at least one user-selectable indicator comprises at least one button.

3. The device as recited in claim 1 wherein the processor causes the device to power off after a predetermined amount of time.

4. The device as recited in claim 3 wherein said predetermined amount of time is less than or equal to 30 minutes.

5. The device as recited in claim 1 further comprising an attachment mechanism configured to allow the user to attach the device to a baby crib.

6. The device as recited in claim 1 wherein said memory is configured to store a log of previous user-selected head positions, further comprising a wireless communications module configured to communicate said log to one or more mobile devices.

7. The device as recited in claim 1 wherein the at least one user-selectable indicator comprises a single button which causes a different one of the plurality of suggested head positions to illuminate each time the button is pressed.

8. The device as recited in claim 1 further comprising a power button, wherein the device is powered on by the user engaging the power button or the reminder button or the user-selectable indicator.

9. A method for regulating and monitoring infant head positions, the method comprising:
  providing a body having a display area displaying a plurality of suggested head positions for the infant;
  selecting manually from the plurality of suggested head positions, using a user-selectable indicator, a first actual head position representing the actual head position in which the infant is placed to rest at a first instance;
  maintaining visual indication, using a source of illumination, of said first actual head position until the user manually selects, using the user-selectable indicator, a second one of the plurality of suggested head positions representing the actual head position in which the infant is placed to rest at a second instance;
  storing in memory the user-selected head position which is visually indicated upon powering off the device;
  causing said source of illumination to blink indicating the user-selected head position stored in said memory upon the device being powered on, said blinking to continue until the user manually selects a different head position using the user-selectable indicator, or until the device is powered off;
  pressing a reminder button to power on the device and causing the device to visually indicate the user-selected head position stored in said memory.

10. A method as recited in claim 9 wherein the user-selectable indicator comprises at least one button.

11. A method as recited in claim 9 wherein the device powers off after a predetermined amount of time.

12. A method as recited in claim 11 wherein said predetermined amount of time is less than or equal to 30 minutes.

13. A method as recited in claim 9 further comprising attaching said body to a baby crib using an integrated attachment mechanism configured for attachment of the body to a baby crib.

14. A method as recited in claim 9 further comprising storing in said memory a log of previous user-selected head positions, and communicating said log to one or more mobile devices via a wireless communications module.

15. A device for regulating and monitoring infant head positions, the device comprising:
  a body;
  a power source;
  said body having a display area displaying a plurality of suggested head positions for the infant;
  said body including at least one user-selectable indicator for selecting a first one of said plurality of suggested head positions representing an actual head position of the infant at a first instance;
  said user-selectable indicator being coupled with a source of illumination for maintaining visual indication of said first one of said plurality of suggested head positions of the infant until the user manually selects a second one of said plurality of suggested head positions representing an actual head position of the infant at a second instance, or until the device is powered off;
  said source of illumination electrically connected to said power source;
  a processor coupled with memory;
  said memory configured to store the user-selected head position which is visually indicated at the time the device is powered off;
  said processor configured to cause said source of illumination to blink indicating the user-selected head position stored in said memory upon the device being powered on, said blinking to continue until the user manually selects a different head position or until the device is powered off;
  said processor configured to cause the device to power off after a predetermined amount of time passes from the time the user selects a different head position.

16. The device as recited in claim 15 wherein the at least one user-selectable indicator comprises at least one button.

17. The device as recited in claim 15 wherein said predetermined amount of time is less than or equal to 30 minutes.

18. The device as recited in claim 15 further comprising an attachment mechanism configured to allow the user to attach the device to a baby crib.

19. The device as recited in claim 15 wherein said memory is configured to store a log of previous user-selected head positions, further comprising a wireless communications module configured to communicate said log to one or more mobile devices.

20. The device as recited in claim 15 wherein the at least one user-selectable indicator comprises a single button which causes a different one of the plurality of suggested head positions to illuminate each time the button is pressed.

* * * * *